US009855055B2

(12) United States Patent
Kosiorek et al.

(10) Patent No.: US 9,855,055 B2
(45) Date of Patent: Jan. 2, 2018

(54) MECHANICAL TOURNIQUET APPARATUS AND METHOD OF USE

(71) Applicants: Christopher B. Kosiorek, La Vernia, TX (US); Dexter C. Drayton, San Antonio, TX (US); Esra Abir, New York, NY (US); Neslihan Damar, Istanbul (TR); Nilufer Polat, Brooklyn, NY (US); Yavuz Avci, Sunnyside, NY (US)

(72) Inventors: Christopher B. Kosiorek, La Vernia, TX (US); Dexter C. Drayton, San Antonio, TX (US); Esra Abir, New York, NY (US); Neslihan Damar, Istanbul (TR); Nilufer Polat, Brooklyn, NY (US); Yavuz Avci, Sunnyside, NY (US)

(73) Assignees: ALPHAPOINTE, Kansas City, MO (US); THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 226 days.

(21) Appl. No.: 14/500,084

(22) Filed: Sep. 29, 2014

(65) Prior Publication Data
US 2015/0094756 A1 Apr. 2, 2015

Related U.S. Application Data

(60) Provisional application No. 61/883,769, filed on Sep. 27, 2013.

(51) Int. Cl.
*A61B 17/00* (2006.01)
*A61B 17/132* (2006.01)

(52) U.S. Cl.
CPC ...... *A61B 17/1327* (2013.01); *A61B 17/1322* (2013.01); *Y10T 29/49826* (2015.01)

(58) Field of Classification Search
CPC ............ A61B 17/1322; A61B 17/1327; A61B 17/132; Y10T 29/49826; Y10T 24/16
See application file for complete search history.

(56) References Cited

U.S. PATENT DOCUMENTS 1,406,770 A 2/1922 Smith
2,084,412 A * 6/1937 Schaefer ................. A41F 15/00
24/186
(Continued)

FOREIGN PATENT DOCUMENTS

CN 201469344 U 5/2010
CN 203169261 U 9/2013
(Continued)

OTHER PUBLICATIONS

Abdominal Aortic Tourniquet, http://www.militarytimes.com/article/20130928/NEWS/309280006/Abdominal-tourniquet-giveslifesaving-time, accessed Oct. 28, 2014.
(Continued)

*Primary Examiner* — Eric Rosen
*Assistant Examiner* — Son Dang
(74) *Attorney, Agent, or Firm* — Kutak Rock LLP; Marcellus A. Chase

(57) ABSTRACT

A pre-fabricated tourniquet that is easy to apply, that ensures consistent and even circumferential pressure, that is light weight, that provides standard life saving operation, and that can be utilized in any setting or situation, and related methods are provided. Mechanically constricting tourniquet apparatus and related methods are provided that are comprised of a tourniquet body, a carriage, a torsion bar, a
(Continued)

receiver and a slider. The tourniquet is long enough to encircle a human limb, for example, an arm or leg.

34 Claims, 4 Drawing Sheets

(56) References Cited

U.S. PATENT DOCUMENTS

| | | | |
|---|---|---|---|
| 2,387,428 A | | 10/1945 | Brothers |
| 2,410,880 A | * | 11/1946 | Hennicke ............... A44B 11/24 24/188 |
| 2,528,078 A | * | 10/1950 | Quilter ................... A44B 11/10 24/171 |
| 2,702,551 A | | 2/1955 | Hobson et al. |
| 3,120,846 A | | 2/1964 | Fletcher |
| 3,165,803 A | * | 1/1965 | Gaylord ............. A44B 11/2526 24/311 |
| 4,102,343 A | | 7/1978 | Schneider |
| 4,273,130 A | * | 6/1981 | Simpson ............ A61B 17/1322 128/DIG. 15 |
| 4,279,367 A | | 7/1981 | Jacobs et al. |
| 4,501,027 A | * | 2/1985 | Olsson .................... A44B 11/28 2/321 |
| 4,640,281 A | | 2/1987 | Sturm et al. |
| 5,304,202 A | | 4/1994 | Stahl |
| 5,372,575 A | | 12/1994 | Sebastian |
| 5,413,582 A | | 5/1995 | Eaton |
| 5,607,448 A | | 3/1997 | Stahl et al. |
| 5,649,954 A | | 7/1997 | McEwen et al. |
| 5,690,672 A | | 11/1997 | Cohen et al. |
| 6,131,972 A | * | 10/2000 | Whitehead ............. B25G 1/102 16/430 |
| 6,682,547 B2 | | 1/2004 | McEwen et al. |
| 6,746,470 B2 | | 6/2004 | McEwen et al. |
| 6,833,001 B1 | | 12/2004 | Chao |
| 6,884,254 B2 | | 4/2005 | Brooks |
| 6,899,720 B1 | | 5/2005 | McMillan |
| 6,960,023 B2 | | 11/2005 | Hsu et al. |
| 6,960,223 B1 | | 11/2005 | Ambach |
| 7,582,102 B2 | | 9/2009 | Heinz et al. |
| 7,776,064 B2 | | 8/2010 | Jennifer et al. |
| 7,842,067 B2 | | 11/2010 | Esposito |
| 7,892,253 B2 | | 2/2011 | Esposito et al. |
| D649,642 S | | 11/2011 | Johnson |
| 8,303,620 B2 | | 11/2012 | Johnson et al. |
| 8,343,182 B2 | | 1/2013 | Kirkham |
| 8,348,970 B2 | | 1/2013 | Janota |
| 8,425,551 B2 | | 4/2013 | McEwen et al. |
| 8,568,341 B2 | | 10/2013 | Flood |
| 8,707,468 B2 | | 4/2014 | Reynolds et al. |
| 8,834,517 B2 | | 9/2014 | Croushorn et al. |
| 8,863,333 B2 | | 10/2014 | Cain et al. |
| 8,926,651 B2 | * | 1/2015 | McDonald ......... A61B 17/1322 606/201 |
| 2003/0028215 A1 | | 2/2003 | Brooks |
| 2005/0240217 A1 | * | 10/2005 | Jennifer ............. A61B 17/1322 606/203 |
| 2005/0267518 A1 | | 12/2005 | Wright et al. |
| 2006/0095072 A1 | | 5/2006 | TenBrink et al. |
| 2007/0038243 A1 | | 2/2007 | Rutherford |
| 2007/0250109 A1 | | 10/2007 | Kerstein et al. |
| 2008/0183207 A1 | | 7/2008 | Horne |
| 2008/0209650 A1 | * | 9/2008 | Brewer ............... A46B 15/0002 15/22.1 |
| 2008/0262534 A1 | | 10/2008 | O'Neil |
| 2009/0024159 A1 | | 1/2009 | Nee et al. |
| 2010/0049241 A1 | | 2/2010 | Persson |
| 2011/0204114 A1 | | 8/2011 | Miller |
| 2011/0307004 A1 | | 12/2011 | Johnson et al. |
| 2011/0313435 A1 | * | 12/2011 | Aldridge ............. A61B 17/823 606/151 |
| 2012/0071917 A1 | | 3/2012 | McDonald et al. |
| 2012/0260463 A1 | * | 10/2012 | Hines ..................... B25G 1/102 16/430 |
| 2013/0012857 A1 | | 1/2013 | Flynn et al. |
| 2013/0110019 A1 | | 5/2013 | Hopman et al. |
| 2013/0110027 A1 | | 5/2013 | Kobler |
| 2013/0145554 A1 | | 6/2013 | Cane et al. |
| 2013/0296921 A1 | | 11/2013 | Saunders et al. |
| 2013/0310872 A1 | | 11/2013 | Croushorn et al. |
| 2014/0277103 A1 † | | 9/2014 | Esposito |
| 2016/0302799 A1 | | 10/2016 | Esposito |

FOREIGN PATENT DOCUMENTS

| | | |
|---|---|---|
| DE | 3232418 A1 | 3/1984 |
| GB | 191102140 A | 0/1912 |
| GB | 190721801 A | 12/1907 |
| GB | 105170 A | 4/1917 |
| GB | 1206605 A | 9/1970 |
| GB | 8324344 | 10/1983 |
| IN | 1702KOL2007 A | 6/2009 |
| WO | 2011001431 A1 | 1/2011 |

OTHER PUBLICATIONS

SAM Junctional Tourniquet, http://sammedical.com/wp-content/uploads/2013/09/SJT-206-BRO-4_web.pdf, accessed Oct. 28, 2014.
SOF Tactical Tourniquet Wide, http://www.tacmedsolutions.com/product/sof-tactical-tourniquet-wide/, accessed Oct. 27, 2014.
Combat Application Tourniquet, http://combattourniquet.com/about/, accessed Oct. 27, 2014.
Kragh Jr. et al., The military emergency tourniquet programs lessons learned with devices and designs. Military Medicine, 2011, vol. 176, No. 10. pp. 1144-1152.
Walters, T.J., et al., Laboratory Evaluation of Battlefield Tourniquets in Human Volunteers. USAISR Technical Report May 2005. Sep. 30, 2005.

\* cited by examiner
† cited by third party

MECHANICAL TOURNIQUET APPARATUS AND METHOD OF USE

CROSS-REFERENCE TO RELATED APPLICATIONS

This application claims priority to U.S. provisional patent application Ser. No. 61/883,769, filed Sep. 27, 2013, the entire disclosure of which is incorporated herein by reference.

GOVERNMENT RIGHTS

This invention was made with government support under W81XWH-12-P-0497 awarded by USA MED RESEARCH ACQ ACTIVITY. The government has certain rights in the invention.

FIELD

Embodiments of the present invention are directed to a mechanical tourniquet and novel blood flow restriction device. In more detail, embodiments of the present invention are directed to an emergency use, pre-fabricated tourniquet used for restricting flow of blood during extreme hemorrhage or exsanguination.

BACKGROUND

Exsanguination or major blood loss has been shown to be the major leading cause of death on the battlefield and directly correlates to major trauma in the civilian sector. Throughout history, tourniquets have been shown to save lives. Several large studies have confirmed the lifesaving benefit and low incidence of complications from pre-hospital use of tourniquets in combat casualties. Furthermore, the civilian Emergency Medical Services have adopted this opinion as well. Tourniquets are frequently used early in the care of trauma casualties because of the immediate lifesaving intervention capability and the speed with which they can be applied. Moreover, tourniquets are the standard of care for the temporary control of life-threatening extremity hemorrhage during the Care Under Fire (CUF) phase of the Tactical Combat Casualty Care (TCCC) in accordance with the Committee for Tactical Combat Casualty Care (CoTCCC) guidelines. These guidelines are becoming the standard of care for treatment of massive hemorrhage across the spectrum of pre-hospital care worldwide.

Due to the nature of traumatic amputation and dismemberment, there is a requirement for application of an emergency tourniquet to be operated by one hand. For a device to be truly operable by only one hand, it must be capable of being placed on an extremity, upper or lower, without having to perform fine motor skill functions. In general, tourniquet operation should not require the use of fine motor skills, regardless of the one-handed operability requirement, because tourniquets are generally only used during periods of extreme duress (i.e., when it is difficult or impossible to expect the use of fine motor skills).

Traditionally, tourniquets were nothing more than a general section of cloth material, usually a cravat, and a stick or dowel used as a windless. The general concept was to tighten the cloth material, reducing the circumference (diameter) of the cloth material against the extremity soft tissue, creating circumferential pressure sufficient enough to occlude blood flow. These make-shift tourniquets were often applied with too much pressure and caused neurovascular damage in limbs. Although the patient's life and limb were saved, the affected limb was permanently damaged. Therefore, a pre-fabricated tourniquet designed for consistent, even circumferential pressure is ideal for emergency use.

There are many situations in which a tourniquet can save a life other than in military applications. Some recreational activities can be inherently dangerous and can cause severe injury requiring the use of such an emergency device, especially in a remote setting. Primary examples of this are camping, rock climbing, hiking, boating, etc. Footprint size and weight are always a consideration in such settings since the individual user is required to carry the device in a backpack. Therefore, a ruggedized pre-fabricated tourniquet made of the strong and light material would be best-suited for the end-user. Such a tourniquet would provide for efficient transportation and effective, life-saving utilization.

Thus, there is a need for a pre-fabricated tourniquet that is easy to apply, that ensures consistent and even circumferential pressure, that is light weight, that provides standard life saving operation, and that can be utilized in any setting or situation.

SUMMARY

One object of the general inventive concept is to provide a mechanically constricting tourniquet apparatus made up of a tourniquet body, a carriage, a torsion bar, a receiver and a slider. The tourniquet body is long enough to encircle a human limb, for example, an arm or leg. The tourniquet body has two ends opposite one another. The tourniquet body has an interior side, intended to be positioned facing toward the limb. Opposite the interior side, the tourniquet body has an exterior side, intended to be positioned facing away from the limb.

Like the tourniquet body, the carriage also has an interior side and an exterior side, with the interior side intended to be positioned facing toward the limb and the exterior side intended to be positioned facing away from the limb. The carriage is attached to the tourniquet body between the two opposing ends of the tourniquet body. The carriage also includes a torsion bar retainer.

A torsion bar is positioned on the exterior side of the tourniquet body and on the exterior side of the carriage. The torsion bar has two opposing ends and a middle portion. The middle portion has a slot sized and shaped such that a tightening strap can slide through the slot. Each of the two opposing ends are sized and shaped such that either can mate with the torsion bar retainer.

A tightening strap is positioned on the exterior side of the tourniquet body and on the exterior side of the carriage. The tightening strap has a middle portion and two opposite ends. The tightening strap is attached to the tourniquet body at each of the opposite ends of the tightening strap. The carriage is positioned between the opposite ends of the tightening strap. The middle portion of the tightening strap passes through the slot of the torsion bar.

A receiver is attached to one end of the tourniquet body. A slider is attached to the tourniquet body and positioned between the carriage and the end of the tourniquet body opposite the end with the receiver attached. The slider is sized and shaped to slide between various positions between the carriage and the end of the tourniquet body. The slider and receiver are sized and shaped to mate with one another. When the torsion bar is rotated, the tightening strap is tightened and the tourniquet body is pulled tighter. The tourniquet body is pulled equally in two opposite directions, toward the carriage.

Another object of the general inventive concept is to provide a method of making a mechanically constricting tourniquet apparatus. The method includes providing a tourniquet body, attaching a carriage, attaching a tightening strap, sliding a tightening strap through a slot in a torsion bar, attaching a receiver to one end of the tourniquet body, and attaching a slider to the tourniquet body.

The tourniquet body is long enough to wrap around a human limb, such as an arm or leg. The tourniquet body has two ends opposite each other. The tourniquet body also has an interior side intended to be positioned facing toward the limb. Opposite the interior side, the tourniquet body has an exterior side, intended to be positioned facing away from the limb.

Like the tourniquet body, the carriage also has an interior side intended to be facing toward the limb and an exterior side opposite the interior side intended to be facing away from the limb. The carriage also includes a torsion bar retainer. The carriage is attached to the tourniquet body such the carriage remains positioned between the two opposing ends of the tourniquet body.

The tightening strap has a middle portion and two opposite ends. The tightening strap is attached to the tourniquet body at each of the opposite ends of the tightening strap and with the carriage positioned between the opposite ends of the tightening strap. The tightening strap is positioned on the exterior side of the tourniquet body and on the exterior side of the carriage.

The torsion bar has two opposing ends and a middle portion. The torsion bar is positioned on the exterior side of the tourniquet body and on the exterior side of the carriage. The middle portion of the torsion bar includes a slot sized and shaped such that the tightening strap can slide through the slot. The tightening strap is slid through this slot. Each of the two opposing ends of the torsion bar are sized and shaped to mate with the torsion bar retainer of the carriage. When the torsion bar is rotated, the tightening strap is tightened and the tourniquet body is pulled tighter. The tourniquet body is pulled equally in two opposite directions, toward the carriage.

A receiver is attached to one end of the tourniquet body. A slider is attached to the tourniquet body between the carriage and the other end of the tourniquet body. The slider can be slid to a plurality of different positions between the carriage and the end of the tourniquet body opposite the receiver. The slider and receiver are sized and shaped to mate with one another.

The foregoing and other objects are intended to be illustrative of the invention and are not meant in a limiting sense. Many possible embodiments of the invention may be made and will be readily evident upon a study of the following specification and accompanying drawings comprising a part thereof. For example, dimensional values included herein are provided for exemplary purposes, and embodiments of the present invention contemplate tourniquets or tourniquet components having a various dimensional values. Furthermore, various features and subcombinations of invention may be employed without reference to other features and subcombinations. Other objects and advantages of this invention will become apparent from the following description taken in connection with the accompanying drawings, wherein is set forth by way of illustration and example, an embodiment of this invention.

DRAWINGS

Embodiments of the invention are set forth herein and are shown in the following drawings.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
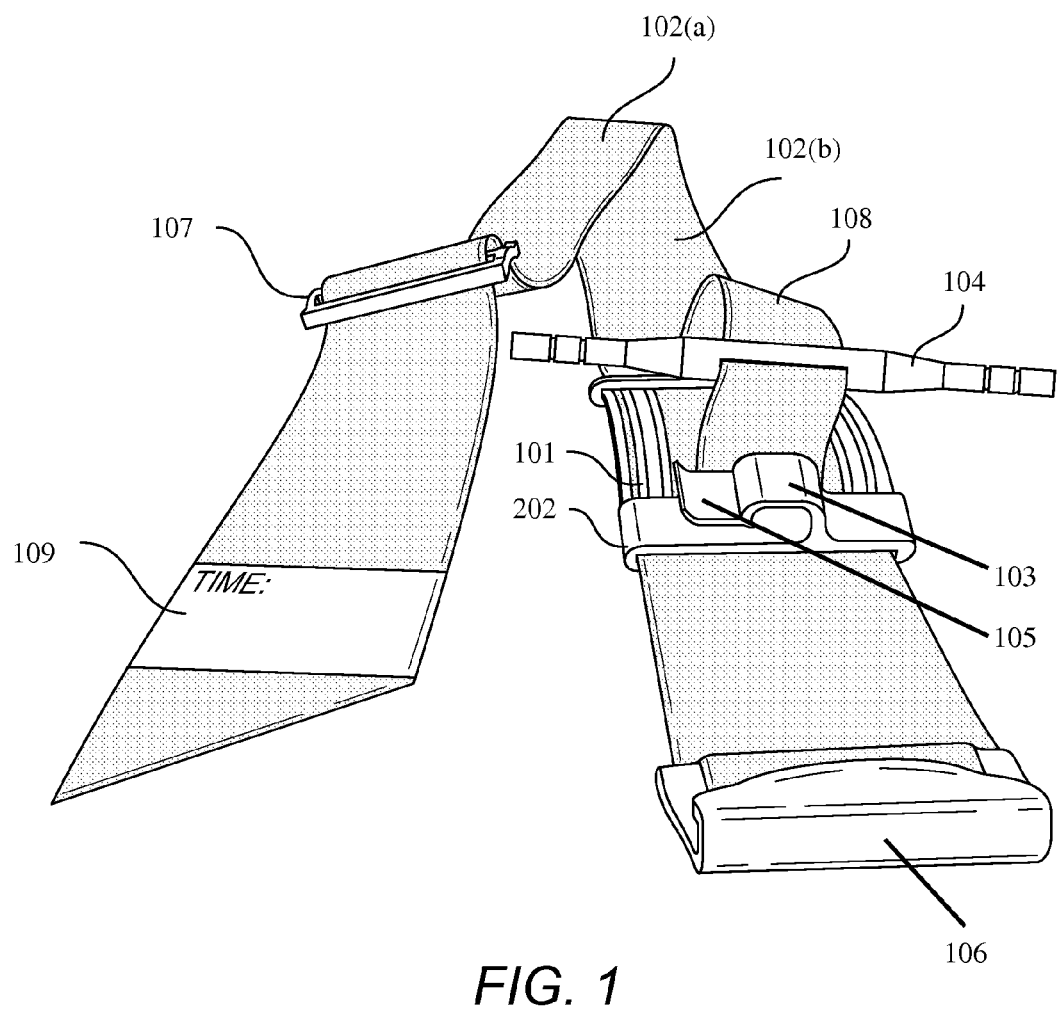
FIG. 1 shows an exemplary mechanical tourniquet according to an embodiment of the general inventive concept.
Figure 6:
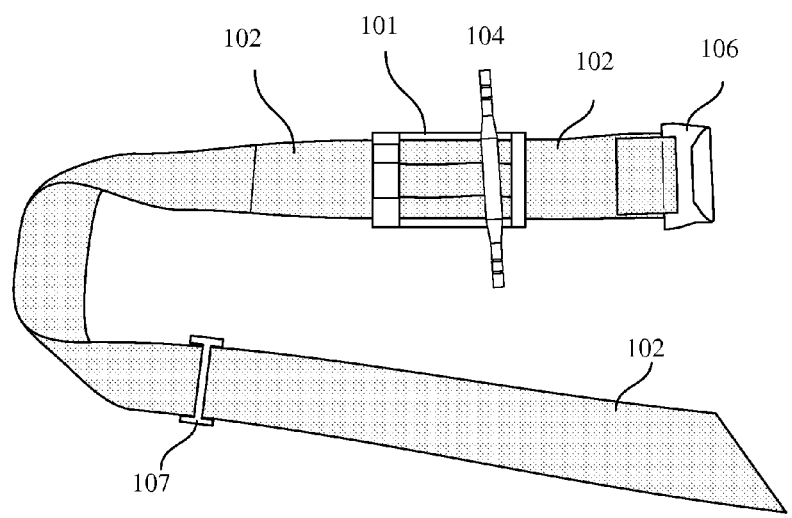
FIG. 6 shows an additional view of the tourniquet from FIG. 1.
Figure 7:
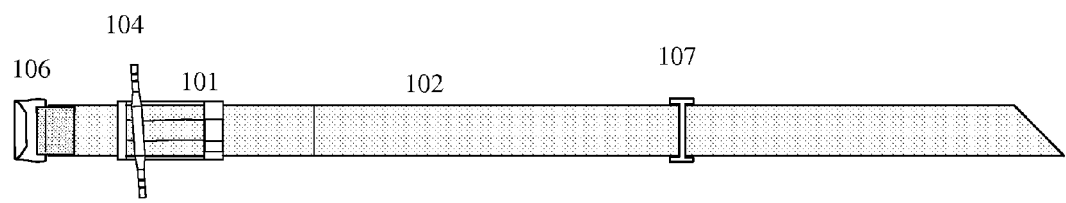
FIG. 7 shows still another view of the tourniquet from FIG. 1.

With reference to FIG. 1, embodiments of the present invention include a tourniquet for restricting a flow of blood in a body part, such as an upper or a lower extremity. In certain embodiments, the tourniquet is comprised of: (a) a carriage 101 (See also FIG. 2) at a central point of a tourniquet body 102, with the carriage 101 acting as an attachment point and as a base plate for mechanical action, and including a torsion bar retainer 103 that holds a torsion bar 104 (See also FIG. 3) in place once tension is created by a twisting action (i.e., twisting or turning the torsion bar), with the torsion bar retainer 103 being releasable upon demand by lifting on a torsion bar retainer release 105; (b) the torsion bar 104 connected to the tourniquet body 102 and acting as a fulcrum to twist a tightening strap 108 so as to shorten a length of a diameter of the tourniquet body 102; (c) a receiver 106 (See also FIG. 4) for accepting a slider 107 (See also FIG. 5) on the tourniquet body 102 from any position along the tourniquet body 102 on a long free running side short of the carriage 101 itself, with the receiver 106 allowing a user to "snap" the slider 107 into place, and furthermore, the receiver 106 is attached to the short end of tourniquet body 102 that runs through the carriage 101; (d) the slider 107 operates as a friction buckle and is positioned along any section of the tourniquet body 102 by being attached to the long free running end of the tourniquet body 102, and furthermore, the slider 107 includes a round side bar and a square side bar with grippers for allowing free rotation when attached to the receiver 106; and (e) the tourniquet body 102 (See also FIGS. 6-7) operating in conjunction with the above-described components (i.e., components a-d). In operation, the tourniquet is operable to create a continuous loop that is placed around an extremity to accomplish circumferential pressure to restrict blood flow. A rotation of the torsion bar 104 through the tightening strap slot shortens the diameter of the continuous loop creating a radial compression force against the extremity.

With respect to the embodiment shown in FIG. 1, the back face of the tourniquet body 102 is shown as 102(a). The back face 102(a) of the tourniquet body 102 is the interior side and is intended to be positioned such that it is facing toward the limb/extremity. In some embodiments, the tourniquet body 102 is comprised of nylon material. The front face of the tourniquet body 102 is shown as 102(b). The front face 102(b) of the tourniquet body 102 is the exterior side and is intended to be positioned such that it is facing away from the limb/extremity. In some embodiments, the front face 102(b) of the tourniquet body 102 includes dual hook and loop fasteners such that the tourniquet body 102 can be attached to itself.

Still referring to FIG. 1, the tightening strap 108 is a strip of material smaller in size than the tourniquet body 102. The tightening strap 108 is connected to the tourniquet body 102 on both sides of the carriage 101. The tightening strap 108 is routed through a slot in the torsion bar 104. The tightening strap 108 provides a constricting action by pulling both sides of the tourniquet body 102 when the torsion bar 104 is twisted.

In some embodiments, the tourniquet body 102 further includes a blank label 109. The blank label 109 may be used to write the time when the tourniquet is applied or various other relevant notes regarding patient care.

In some embodiments, the carriage 101 includes a strap holder to hold the tourniquet body 102 stable when operating the tourniquet.

In more detail, and with reference to FIGS. 1, 2, and 6-7, the carriage 101 will act as the base for the action of twisting the torsion bar 104. In some embodiments, the carriage 101 has both a niche 201 and a narrow 210 bridge at either end of the carriage base itself, for allowing the tourniquet body 102 strap material to move efficiently through and in line when turning the torsion bar 104. The carriage 101 is ruggedized for durability but has, in some embodiments, a flex and gradual curve that provides the carriage 101 with the ability to conform to both small and large limbs. As such, the carriage 101 allows for application on both upper and lower extremities regardless of size or composition of the extremities to which the tourniquet is being applied. In some embodiments, the tourniquet will be capable of being applied to adult human beings with extremities that are sized between the $5^{th}$ to $95^{th}$ percentile.

Figure 2:
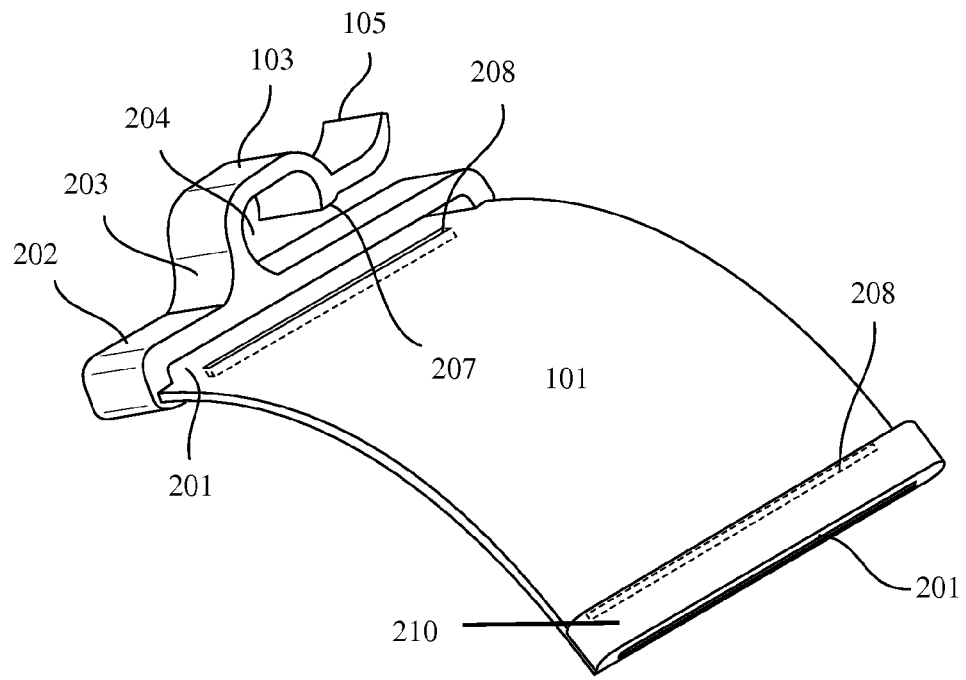
FIG. 2 shows an exemplary carriage of the tourniquet from FIG. 1.

Referring to FIG. 2, the carriage 101 includes a niche 201 at either end of the carriage 101. The niche 201 is sized and shaped to allow the tourniquet body 102 to move easily through the niche 201 when the torsion bar 104 is twisted. In some embodiments, a niche 201 is included on both ends of the carriage 101. The niche 201 allows the tourniquet body 102 to pass through the bridges (202 and 210) and helps to squeeze the tourniquet. In some embodiments, the carriage includes a wide bridge 202 and a narrow bridge 210. The narrow bridge 210 allows for easy travel of the tourniquet body 102 through the carriage 101 as the tourniquet is tightened. The wide bridge 202 holds the torsion bar retainer 103 and provides space for a niche 201. The wide bridge 202 and niche 201 provide a "tunnel" passage for the tourniquet body 102 to pass through as the tourniquet is tightened. A torsion bar retainer supporter 203 connects the torsion bar retainer 103 to the wide bridge 202. The torsion bar retainer supporter 203 prevents diffraction of the retainer 103 when the torsion bar 104 is released.

Still referring to FIG. 2, when the torsion bar 104 is twisted and the tourniquet body 102 is drawn in, an end of the torsion bar 104 is placed into the torsion bar retainer 103 and is held secure in a torsion bar space 204. An end of the torsion bar 104 is placed into the torsion bar space 204 after the torsion bar 104 is twisted. The torsion bar 104 is held in place by the torsion bar retainer 103 so that circumferential pressure remains stable. In some embodiments, the torsion bar retainer 103 includes a spur 207 to better secure the torsion bar 104 in place in the retainer 103. The torsion bar retainer release 105 provides a mechanism of mechanical movement to release the torsion bar 104 from the retainer 103.

Still referring to FIG. 2, in some embodiments, the carriage 101 includes one or more holder slots 208. The holder slots 208 are spaces for carriage holders to hold the carriage in place. In some embodiments, the carriage 101 includes a base plate for the torsion bar 104 and torsion bar retainer 103. As the torsion bar 104 is twisted, the base plate provides structure to absorb and disperse forces circumferentially. The base plate assists in application and tightening of the torsion bar 103. In some embodiments, the base plate has a slight curvature. In some embodiments, the base plate has an approximately 33 degree inclination. In additional embodiments, and with reference to FIGS. 1-3, and 6-7, the torsion bar retainer 103 of the carriage 101 is operable for retaining either end of the torsion bar 104 once circumferential pressure is applied (i.e., by turning/twisting the torsion bar 104). The torsion bar 104 is held in place by a spur 207 affixed to the tip of the retainer 103. Furthermore, the torsion bar retainer 103 includes a torsion bar retainer release 105, which provides better movement and application for releasing the retained torsion bar 104 while under pressure. The torsion bar retainer 103 is integrally formed with the carriage 101 by the torsion bar retainer supporter 203 which prevents breakage and diffraction when retaining or releasing the torsion bar.

Figure 3:
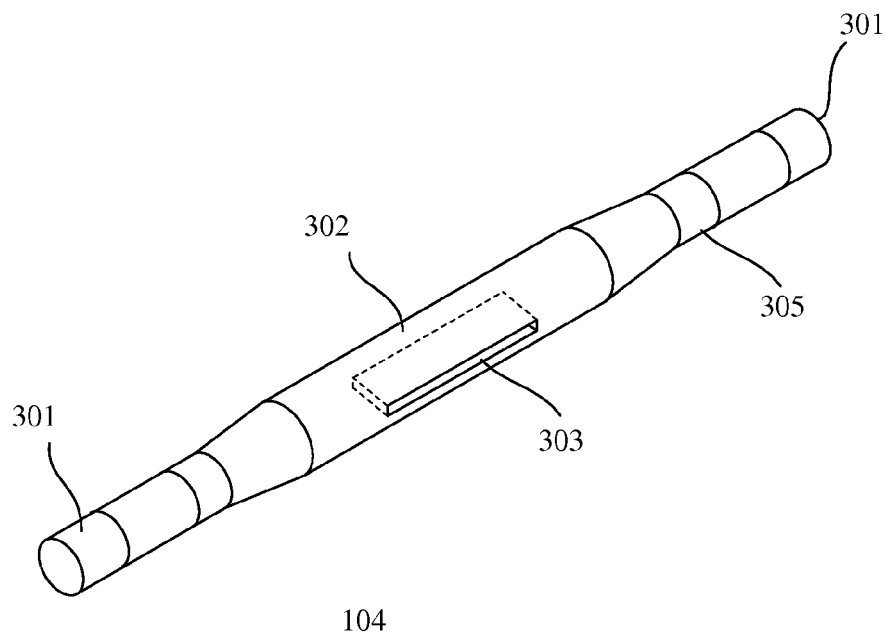
FIG. 3 shows an exemplary torsion bar of the tourniquet from FIG. 1.

Referring to FIG. 3, the torsion bar 104 of an embodiment is shown. The torsion bar 104 includes an end portion 301 at both ends. The end portion 301 is the part of the torsion bar 104 that is placed into the torsion bar space (204 of FIG. 2) to hold the torsion bar 104 in place. The torsion bar 104 also includes a middle portion 302 that is thicker than the end portion 301. The middle portion 302 supports the tightening strap slot 303. The middle portion 302 is sized and shaped to reduce the chance of failure of the torsion bar 104 during application and tightening of the tourniquet. The tightening strap slot 303 is a slot in the middle portion 302 of the torsion bar 104 through which the tightening strap (108 of FIG. 1) is routed. In some embodiments, the torsion bar 104 is circular in cross section with a preferred diameter of approximately 0.3 inches. In some embodiments, the torsion bar 104 includes torsion bar grips 305, which are checker-board-style grooves to improve friction, grip, and tactile sensitivity when applying the tourniquet.

Furthermore, with reference to FIGS. 1-2, and 6-7, the carriage plate of the carriage 101 has holder slots 208 to secure the carriage 101 to the tourniquet body 102 and to hold the carriage 101 in place during use of the tourniquet.

With reference to FIG. 1, additional embodiments of the present invention include a tourniquet for restricting a flow of blood in a body part, such as an upper or a lower extremity, with the tourniquet comprising: (a) a short end (See also FIGS. 6-7) of a tourniquet body 102 attached to a carriage 101 (See also FIG. 2); (b) a long running end of the tourniquet body 102 attached to the carriage 101, furthermore a receiver 106 (See also FIG. 4) and a slider 107 (See also FIG. 5) are capable of being secured together so as to anchor the long running end of the tourniquet body 102 to the short end of the tourniquet body 102 near where the carriage 101 is attached to the tourniquet body 102, furthermore still, the slider 107 allows for positional adjustment anywhere along the long running end of the tourniquet body 102 short of the carriage attachment point itself; (c) the tourniquet body 102 connects with the carriage 101 at an attachment point of the tourniquet body 102, with the connection being achieved by two holder slots 208 of the carriage, with such holder slots 208 being integrally formed with the carriage 101 (such as by a continuous mold), and as such, the tourniquet body 102 extends through the carriage 101 in a generally continuous manner, furthermore still, the tourniquet body 102 does not contain any breaks throughout its entire length, thus creating a continuous loop of tourniquet body 102, and furthermore still, the only attachment point of the continuous, tourniquet body 102 loop is where the tourniquet body 102 is attached to the receiver 106; (d) a tightening strap 108 (See also FIGS. 6-7) attached to the short end and long free running end of the tourniquet body 102, with the tightening strap 108 running through a middle portion 302 of a torsion bar 104 (See also FIG. 3), and with the tightening strap 108 functioning as a shortening action mechanism of the tourniquet body 102, when twisted by way of the torsion bar 104; (e) the mechanical shortening action is performed by pulling together (i.e., a shortening) the short and free running long end of the tourniquet body 102 over the carriage 101, through the niche 201 and narrow bridge 210, by way of the tightening strap 108, so as to create a circumferential pressure of the continuous tourniquet body 102 loop around an extremity.

In certain embodiments, the tourniquet includes a torsion bar 104 (See FIG. 3) that is approximately 0.3 inches in diameter and comprised of one middle 302 and two end portions 301. The diameter of the torsion bar 104 allows for ease and non-restrictive placement and allows for simple release of the torsion bar retainer 103. A middle portion 302 of the torsion bar 104 includes a tightening strap slot 303 where the tightening strap 108 is secured in place ensuring tourniquet body shortening action when the torsion bar 104 is twisted and pressure is applied. Furthermore, the torsion bar 104 includes torsion bar grips 305 that are grooved into the end portions 301 of the torsion bar 104 to increase tactile sensitivity. The middle portion 302 of the torsion bar 104 also has a textured rough surface to decrease the possibility of slippage when applying pressure during the mechanism of action.

Figure 4:
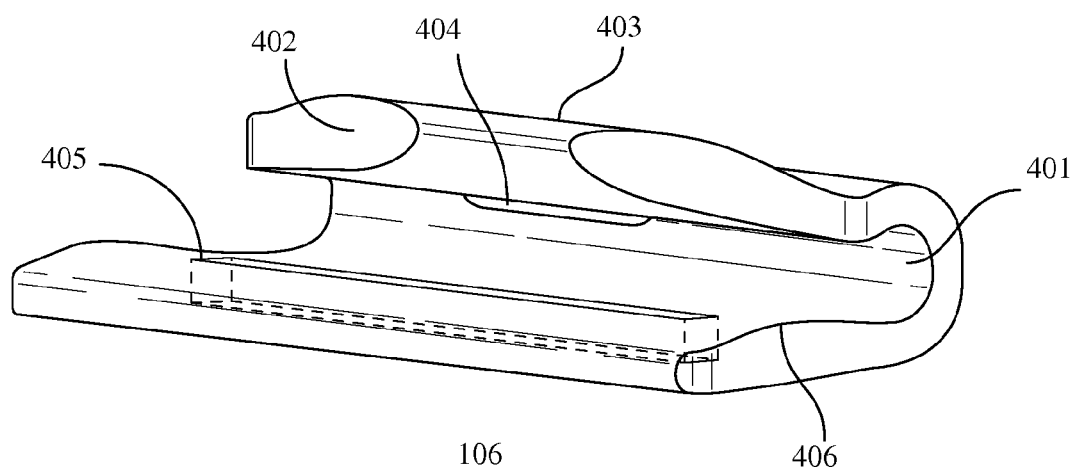
FIG. 4 shows an exemplary receiver of the tourniquet from FIG. 1.

As illustrated in FIG. 4, the receiver 106 includes a hook-shaped catch 401 that the round side bar 501 of the slider 107 (See FIG. 5) can be place into or removed from by the user on demand through application of the receiver flange 402. A lip portion 403 of the receiver 106 is the narrower portion of the receiver 106 and facilitates ease of placement for the round side bar 501 of the slider 107, and the bar locks the hook slider into place.

With respect to FIG. 4, in some embodiments, the hook-shaped catch 401 (or slider niche) is sized and shaped to mate with and receive the slider 107 and lock the slider 107 securely in place. The receiver flange 402 guides and provides an easy placement for the slider 107 which locks the tourniquet body in place. The flange 402 slopes upward to facility placement. The lip 403 is a narrower part of the receiver 106 to provide an easy placement with the receiver flange 402 for the slider 107. A bar 404 hangs down from the lip 403. The bar 404 supports locking of the hook slide and prevents unintentional displacement (dislodging) of the slider 107 from the receiver 106. The bar 404 allows the slider 107 to "snap" or audibly "click" when the slider 107 and receiver 106 are properly mated. A supporter 406 is a thicker portion of the receiver 106 that structurally supports the receiver slot 405. The receiver slot 405 is a space for a receiver holder to connect the receiver 106 to the tourniquet body 102.

Figure 5:
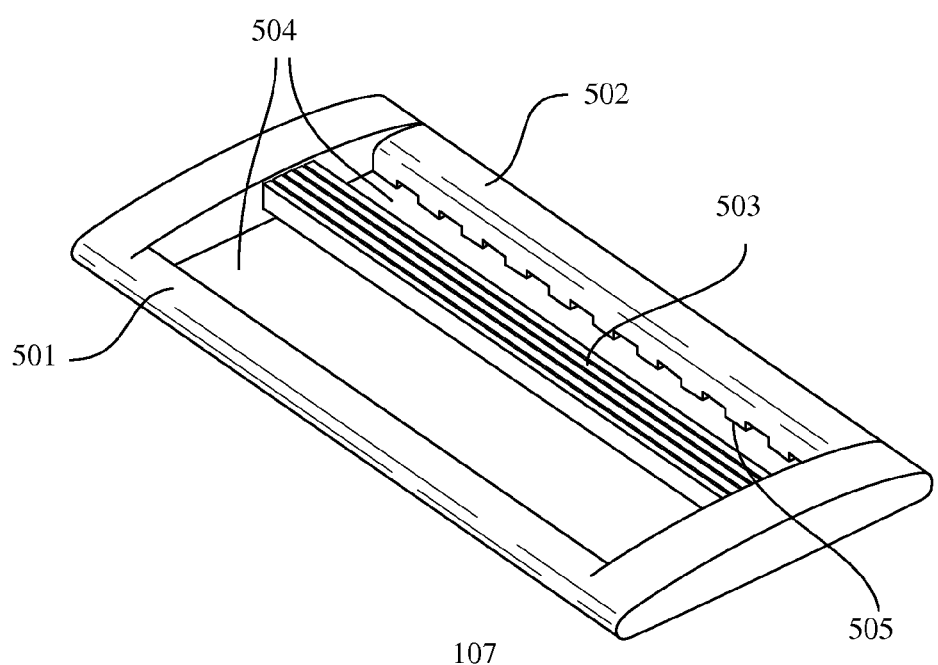
FIG. 5 shows an exemplary slider of the tourniquet from FIG. 1.

With reference to FIG. 5, the slider 107 functions as a friction buckle that is operable to be placed anywhere on the tourniquet long body 102 free running end of the tourniquet, short of the carriage attachment hook. The square side bar 502 of the slider 107 with protruding grippers 505 facilitates friction when the round side bar 501 is placed into the receiver 106 (See FIG. 4), thus stopping slippage, yet allowing excess slack to be removed from the diameter of the circumferential tourniquet body 102 upon demand from the user with an upward pulling motion of the tourniquet long body. Furthermore, the tourniquet long body 102 can be pre-routed through the slider 107, thus avoiding the necessity to route the long free running end of the tourniquet body 102 through the slider 107 during use.

With respect to FIG. 5, in some embodiments, the slider 107 includes a round edge 501 (or round side bar). The round side bar 501 is sized and shaped to interface with the receiver 106. The round side bar 501 is sized and shaped to allow for articulation when mated with the receiver 106. The slider 107 further includes a frame 502 (or square side bar). The square side bar 502 gives support, structure and shape to the slider 107. In some embodiments, the slider 107 will be a distinctive color to easily and quickly visually distinguish the slider's position relative to the tourniquet body 102. For example, in some embodiments, the slider 107 is coyote brown. In some embodiments, the slider 107 includes a slider friction bar 503. The slider friction bar 503 provides friction and inhibits the release of tension when the tourniquet is applied. The friction bar 503 is positioned higher than the side bars 501 and 502. The friction bar 503 is sized and shaped to lock the slider 107 in position when the tourniquet is applied. The slider 107 further includes slider gaps 504. The tourniquet body 102 is routed through the slider gaps 504 with dual hook and loop fasteners on the tourniquet body 102 side that faces toward the slider friction bar 503. The square side bar 502 of the slider 107 also includes grippers 505. The grippers 505 facilitate friction when the round slider bar 501 is placed into the receiver 106. This stops slippage, yet allows excess slack to be removed from the tourniquet body 102 continuous loop upon demand with an upward pulling motion of the tourniquet body 102 long running end.

Together, the slider 107 (See FIG. 5) and the receiver 106 (See FIG. 4) function as a buckle to attach the tourniquet long body free running end and the tourniquet short body end of the tourniquet, so as to create a continuous loop. Adjustments can be made, via the slider 107, for shortening or lengthening the continuous loop once applied, and/or the slider 107 can be attached or detached from the receiver 106 to facilitate ease of application by the user.

With reference to FIG. 1, further embodiments of the present invention include tourniquet designed for restricting a flow of blood in a body part, such as an upper or a lower extremity, with the tourniquet comprising: (a) a tourniquet body 102 (See also FIGS. 6-7) that is approximately 2 inches wide by approximately 39 inches long, after attachment of the receiver 106 (See also FIG. 4) and the carriage 101 (See also FIG. 2), with such a length including a length of the receiver 106 itself; (b) the tourniquet body 102 includes a front face of a material having dual hook and loop, which allows an excess portion of the long free running end to attach back onto itself once applied, furthermore, the dual hook and loop assists in securing the long free running end of the tourniquet body 102 on the free running side of the slider (See also FIG. 5) creating additional friction and a locking mechanism, furthermore still, a slider friction bar 503 of the slider 107 and the dual hook and loop serve as a two piece locking mechanism when applied as described herein; (c) a tightening strap 108 (See also FIGS. 6-7) is routed through a torsion bar slot 303 of a torsion bar 104 (See also FIG. 3) and connects the short end and long free running end of the continuous loop. The tightening strap 108 is the mechanism of action, such that twisting the torsion bar 104 provides constriction by pulling both sides of the tourniquet body 102 during the application of the tourniquet.

The width of the tourniquet (See FIGS. 1 and 6-7) increases circumferential compression of the soft tissue on the extremity, thus promoting effective occlusion of vessels and achieving better restriction of blood flow, while reducing the amount of circumferential pressure required within the band of the tourniquet. In some embodiments, the 2 inch width of the tourniquet provides an optimal width for functionality, efficacy, weight and cube. The tourniquet body 102 may, in some embodiments, be made from various types of elastic and/or inelastic flexible material, such as woven fabric, vinyl, leather, neoprene, nylon, etc. Furthermore, other components of the tourniquet (e.g., carriage 101, receiver 106, slider 107, torsion bar 104) may be made from rigid or semi-rigid materials, such as various types plastics, metals, or the like.

Furthermore, the slider 107 (See FIG. 5) and the receiver 106 (See FIG. 4) combine to function as a buckle device that can be easily attached and detached to facilitate application on upper or lower extremities. When seated in the receiver 106, the round side bar 501 of the slider 107 pivots, allowing for ease of tightening the free long running end of tourniquet body 102 through the slider 107 and allowing for rapid sizing of the tourniquet on an upper or a lower extremity.

While the present general inventive concept has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

It is also to be understood that the following claims are intended to cover all of the generic and specific features of the invention herein described, and all statements of the scope of the invention which, as a matter of language, might be said to fall therebetween. Hence, the proper scope of the present general inventive concept should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. A blood-flow restriction tourniquet apparatus comprising:
   a tourniquet body having a length sufficient to encircle a human limb, two opposing ends, an interior side and an exterior side opposite the interior side;
   a carriage having an interior side and an exterior side opposite the interior side, the carriage attached to the tourniquet body with the carriage interior side aligned with the tourniquet body interior side and the carriage exterior side aligned with the tourniquet body exterior side and the carriage including a torsion bar retainer;
   a torsion bar positioned on the exterior side of the tourniquet body and on the exterior side of the carriage, the torsion bar having two opposing ends and a middle portion, the middle portion having a slot, and each of the two opposing ends sized and shaped to mate with the torsion bar retainer;
   a tightening strap having a middle portion and two opposite ends, the tightening strap positioned on the exterior side of the tourniquet body and on the exterior side of the carriage, each of the opposite ends of the tightening strap attached to the tourniquet body at opposite ends of the carriage with the carriage positioned between the opposite ends of the tightening strap, the middle portion of the tightening strap passing through the slot of the torsion bar;
   a receiver attached to one end of the tourniquet body; and
   a slider attached to the tourniquet body and positioned between the carriage and the end of the tourniquet body opposing the end with the receiver attached, the slider being sized and shaped such that the slider can be positioned at any one of a plurality of positions between the carriage and the end of the tourniquet body opposing the end with the receiver attached, and the slider and receiver sized and shaped to mate with one another;
   wherein when the torsion bar is rotated, the tightening strap is tightened and the tourniquet body is pulled in two opposite directions, equally, toward the carriage.

2. The blood-flow restriction tourniquet apparatus of claim 1, wherein the slider includes a round side bar and a square side bar with a plurality of grippers.

3. The blood-flow restriction tourniquet apparatus of claim 1, wherein when the slider and receiver are mated together, a continuous loop is created that, when placed around a limb, establishes circumferential pressure around the limb.

4. The blood-flow restriction tourniquet apparatus of claim 3, wherein when the torsion bar is rotated, the tightening strap shortens the diameter of the continuous loop creating a radial compression force sufficient to restrict blood flow in the limb.

5. The blood-flow restriction tourniquet apparatus of claim 1, wherein the carriage includes a niche and a narrow bridge at either end of the carriage, for allowing the tourniquet body to move efficiently through and in line when turning the torsion bar.

6. The blood-flow restriction tourniquet apparatus of claim 1, wherein the torsion bar retainer includes a torsion bar retainer release.

7. The blood-flow restriction tourniquet apparatus of claim 1, wherein the carriage includes one or more holder slot to secure the carriage to the tourniquet body and to hold the carriage in place during use of the tourniquet.

8. The blood-flow restriction tourniquet apparatus of claim 1, wherein the torsion bar includes torsion bar grips that are grooved into the end portions of the torsion bar.

9. The blood-flow restriction tourniquet apparatus of claim 1, wherein the middle portion of the torsion bar includes a textured rough surface.

10. The blood-flow restriction tourniquet apparatus of claim 1, wherein the receiver includes a hook-shaped catch into which the slider can be placed or removed.

11. The blood-flow restriction tourniquet apparatus of claim 10, wherein a lip portion of the receiver is narrower than the receiver and facilitates ease of placement of the slider and locks the hook-shaped catch and slider into place.

12. The blood-flow restriction tourniquet apparatus of claim 1, wherein the tourniquet body is comprised of woven fabric, vinyl, leather, neoprene, or nylon.

13. The blood-flow restriction tourniquet apparatus of claim 1, wherein one of the carriage, receiver, slider or torsion bar is comprised of plastic or metals.

14. The blood-flow restriction tourniquet apparatus of claim 1, wherein the torsion bar is held in place by a spur affixed to a tip of the retainer.

15. The blood-flow restriction tourniquet apparatus of claim 1, wherein the tourniquet body includes dual hook and loop fasteners such that the tourniquet body can be attached to itself.

16. The blood-flow restriction tourniquet apparatus of claim 1, wherein a snap or click audible to a user confirms to the user when the slider and receiver are properly mated with one another.

17. The blood-flow restriction tourniquet apparatus of claim 1, wherein tactile feedback confirms to a user when the slider and receiver are properly mated with one another.

18. A method of making a blood-flow restriction tourniquet apparatus, the method comprising:
providing a tourniquet body, the tourniquet body having a length sufficient to encircle a human limb, the tourniquet body having two opposing ends, an interior side and an exterior side opposite the interior side;
attaching a carriage, the carriage having an interior side, an exterior side opposite the interior side and a torsion bar retainer, to the tourniquet body with the carriage interior side aligned with the tourniquet body interior side and the carriage exterior side aligned with the tourniquet body exterior side;
attaching a tightening strap, the tightening strap having a middle portion and two opposite ends, to the tourniquet body at each of opposite ends of the carriage with the carriage positioned between the opposite ends of the tightening strap, the tightening strap positioned on the exterior side of the tourniquet body and on the exterior side of the carriage;
sliding the middle portion of the tightening strap through a slot in a middle portion of a torsion bar having two opposing ends and the middle portion, the torsion bar being positioned on the exterior side of the tourniquet body and on the exterior side of the carriage, and each of the two opposing ends of the torsion bar being sized and shaped to mate with the torsion bar retainer of the carriage;
attaching a receiver to one end of the tourniquet body; and
attaching a slider to the tourniquet body positioned between the carriage and the end of the tourniquet body opposing the end with the receiver attached, the slider being sized and shaped such that the slider can be positioned at any one of a plurality of positions between the carriage and the end of the tourniquet body opposing the end with the receiver attached, and the slider and receiver sized and shaped to mate with one another;
wherein when the torsion bar is rotated, the tightening strap is tightened and the tourniquet body is pulled in two opposite directions, equally, toward the carriage.

19. The method of claim 18, wherein the slider includes a round side bar and a square side bar with a plurality of grippers.

20. The method of claim 18, wherein when the slider and receiver are mated together, a continuous loop is created that, when placed around a limb, establishes circumferential pressure around the limb.

21. The method of claim 20, wherein when the torsion bar is rotated, the tightening strap shortens the diameter of the continuous loop creating a radial compression force sufficient to restrict blood flow in the limb.

22. The method of claim 18, wherein the carriage includes a niche and a narrow bridge at either end of the carriage, for allowing the tourniquet body to move efficiently through and in line when turning the torsion bar.

23. The method of claim 18, wherein the torsion bar retainer includes a torsion bar retainer release.

24. The method of claim 18, wherein the carriage includes one or more holder slot to secure the carriage to the tourniquet body and to hold the carriage in place during use of the tourniquet.

25. The method of claim 18, wherein the torsion bar includes torsion bar grips that are grooved into the end portions of the torsion bar.

26. The method of claim 18, wherein the middle portion of the torsion bar includes a textured rough surface.

27. The method of claim 18, wherein the receiver includes a hook-shaped catch into which the slider can be placed or removed.

28. The method of claim 27, wherein a lip portion of the receiver is narrower than the receiver and facilitates ease of placement of the slider and locks the hook-shaped catch and slider into place.

29. The method of claim 18, wherein the tourniquet body is comprised of woven fabric, vinyl, leather, neoprene, or nylon.

30. The method of claim 18, wherein one of the carriage, receiver, slider or torsion bar is comprised of plastic or metals.

31. The method of claim 18, wherein the torsion bar is held in place by a spur affixed to a tip of the retainer.

32. The method of claim 18, wherein the tourniquet body includes dual hook and loop fasteners such that the tourniquet body can be attached to itself.

33. The method of claim 18, wherein a snap or click audible to a user confirms to the user when the slider and receiver are properly mated with one another.

34. The method of claim 18, wherein tactile feedback confirms to a user when the slider and receiver are properly mated with one another.

* * * * *